United States Patent
Nasiraei Moghaddam

(10) Patent No.: US 9,933,502 B2
(45) Date of Patent: Apr. 3, 2018

(54) CARDIAC MRI CURVILINEAR TAGGING

(71) Applicant: THE REGENTS OF THE UNIVERSITY OF CALIFORNIA, Oakland, CA (US)

(72) Inventor: Abbas Nasiraei Moghaddam, Porter Ranch, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1289 days.

(21) Appl. No.: 13/949,045

(22) Filed: Jul. 23, 2013

(65) Prior Publication Data
US 2013/0320978 A1 Dec. 5, 2013

Related U.S. Application Data

(63) Continuation of application No. PCT/US2012/023726, filed on Feb. 3, 2012.
(Continued)

(51) Int. Cl.
*G01R 33/54* (2006.01)
*G01R 33/563* (2006.01)
(Continued)

(52) U.S. Cl.
CPC ..... *G01R 33/543* (2013.01); *G01R 33/56333* (2013.01); *A61B 5/0044* (2013.01); *A61B 5/055* (2013.01)

(58) Field of Classification Search
CPC G01R 33/543; G01R 33/56333; A61B 5/055; A61B 5/0044
See application file for complete search history.

(56) References Cited

U.S. PATENT DOCUMENTS 4,516,075 A * 5/1985 Moran .................. A61B 5/055
324/306
4,654,591 A * 3/1987 Moran ................. G01R 33/563
324/306
(Continued)

FOREIGN PATENT DOCUMENTS

WO 2012/106574 A2 8/2012

OTHER PUBLICATIONS

European Patent Office, Supplemental Search Report (ESSR) issued on Mar. 3, 2015 for corresponding European Patent Application No. 12741888.7 (pp. 1-7) and pending claims (8-10) pp. 1-10.
(Continued)

*Primary Examiner* — Dixomara Vargas
(74) *Attorney, Agent, or Firm* — O'Banion & Ritchey LLP; John P. O'Banion

(57) ABSTRACT

A preparation sequencing system and methods are disclosed for generating curvilinear taglines of altered magnetization in an imaging plane of an NMR image. A preparation sequencing module is disclosed for generating a sinusoidal gradient signal simultaneously with a continuous a radio frequency (RF) signal, wherein the sinusoidal gradient signal is shaped to generate a rotating on-resonance excitation plane such that each point in the imaged target volume is on-resonance at least once in a period corresponding to one full rotation of the excitation plane. The on-resonance excitation plane is configured to simultaneously generate a plurality of curvilinear or circular taglines of altered magnetization in the imaging plane.

32 Claims, 12 Drawing Sheets

Related U.S. Application Data

(60) Provisional application No. 61/439,292, filed on Feb. 3, 2011.

(51) Int. Cl.
*A61B 5/00* (2006.01)
*A61B 5/055* (2006.01)

(56) References Cited

U.S. PATENT DOCUMENTS

| | | | | |
|---|---|---|---|---|
| 4,697,149 | A * | 9/1987 | Moran | G01R 33/563 324/306 |
| RE32,701 | E * | 6/1988 | Moran | G01R 33/56308 324/306 |
| 4,953,554 | A | 9/1990 | Zerhouni et al. | |
| 5,054,489 | A | 10/1991 | Axel et al. | |
| 5,111,820 | A | 5/1992 | Axel et al. | |
| 5,217,016 | A | 6/1993 | Axel et al. | |
| 5,270,653 | A * | 12/1993 | Pauly | G01R 33/446 324/309 |
| 5,560,360 | A * | 10/1996 | Filler | 324/307 |
| 5,592,085 | A * | 1/1997 | Ehman | A61B 5/055 324/307 |
| 5,825,186 | A * | 10/1998 | Ehman | A61B 5/055 324/307 |
| 6,453,187 | B1 | 9/2002 | Prince et al. | |
| 6,856,132 | B2 * | 2/2005 | Appel | G01V 3/32 324/303 |
| 6,892,089 | B1 | 5/2005 | Prince et al. | |
| 7,375,522 | B2 * | 5/2008 | Reeder | G01R 33/4828 324/307 |
| 7,619,411 | B2 * | 11/2009 | Reeder | G01R 33/4824 324/309 |
| 8,073,523 | B2 | 12/2011 | Moghaddam | |
| 8,159,222 | B2 * | 4/2012 | King | G01R 33/3415 324/307 |
| 8,727,998 | B2 * | 5/2014 | Yin | A61B 5/055 600/485 |
| 2008/0009704 | A1 | 1/2008 | Morteza et al. | |
| 2008/0269595 | A1 | 10/2008 | Wong | |
| 2010/0014735 | A1 | 1/2010 | Bi et al. | |
| 2010/0063380 | A1 | 3/2010 | Duerk et al. | |

OTHER PUBLICATIONS

Moghaddam et al. "CMR tagging in the polar coordinate system," Journal of Cardiovascular Magnetic Resonance, vol. 13, (Feb. 2, 2011), pp. 27.

Moghaddam et al. "Measuring the myocardial angular information through the Radical Tagging," Proc. Intl. Soc. Mag. Reson. Med., (May 1, 2010) p. 3572.

Moghaddam et al. "CIRcumferential COMpression Encoding (CIRCOME)," Proc. Intl. Soc. Mag. Reson. Med. (May 19, 2007) p. 2515.

Korean International Property Office International Search Report and Written Opinion dated Jul. 23, 2012 for corresponding International Patent Application No. PCT/US2012/023726 (International Patent Application Publication No. WO 2012/106574) (pp. 1-8) with claims searched (pp. 9-14) pp. 1-14.

Spiegel, M., et al. "RingTag: ring-shaped tagging for myocardial centerline assessment." Invest Radiol Oct. 2003, 38(10):669-78.

L. Axel and L. Dougherty, "MR imaging of motion with spatial modulation of magnetization," Radiology, 171: 841-845 (1989).

Bolster B.D., McVeigh E.R., and Zerhouni E.A., "Myocardial Tagging in Polar Coordinates with Use of Striped Tags," Radiology, 177(3): 769-772 (1990).

Pauly J., Nishimura D., and Macovski A., "A linear class of large-tip-angle selective excitation pulses" J. Magn. Reson., 82: 571-587 (1989).

Zerhouni E.A. et al, "Human heart: tagging with MR imaging—a method for noninvasive assessment of myocardial motion," Radiology, 169: 59-63 (1988).

NV Tsekos et al, "Myocardial tagging with B1 insensitive adiabatic DANTE inversion sequences," Magnetic Resonance in Medicine, 34: 395-401 (1995).

* cited by examiner

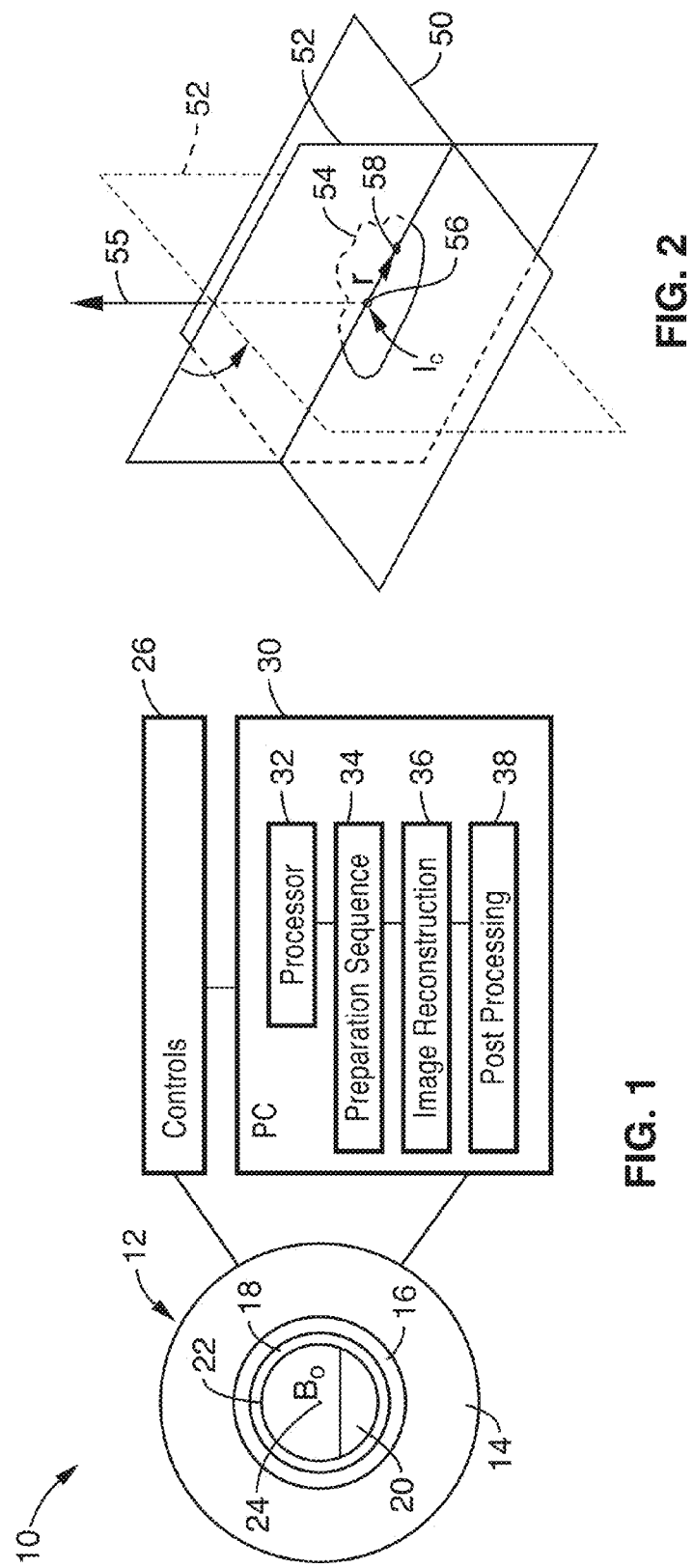

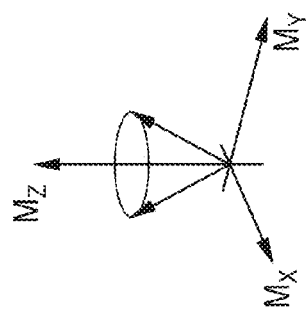
FIG. 5A (Prior Art)
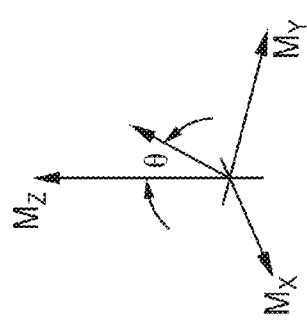
FIG. 5B (Prior Art)
FIG. 5C (Prior Art)
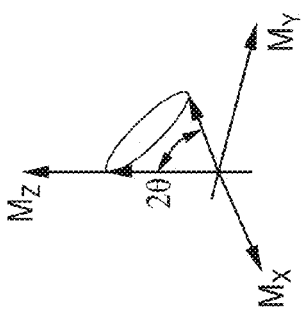
FIG. 5D (Prior Art)
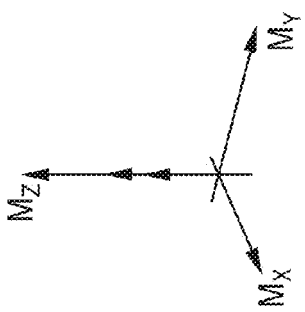
FIG. 5E (Prior Art)

CARDIAC MRI CURVILINEAR TAGGING

CROSS-REFERENCE TO RELATED APPLICATIONS

This application is a 35 U.S.C. § 111(a) continuation of PCT international application number PCT/US2012/023726 filed on Feb. 3, 2012, incorporated herein by reference in its entirety, which is a nonprovisional of U.S. provisional patent application Ser. No. 61/439,292 filed on Feb. 3, 2011, incorporated herein by reference in its entirety. Priority is claimed to each of the foregoing applications.

The above-referenced PCT international application was published as PCT International Publication No. WO 2012/106574 on Aug. 9, 2012 and republished on Sep. 20, 2012, and is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant

BACKGROUND OF THE INVENTION

1. Technical Field

This invention pertains generally to magnetic resonance imaging (MRI), and more particularly to cardiac MRI (CMR) tagging.

2. Background

Cardiac MRI tagging is a promising technique for studying regional heart wall motion noninvasively (both at rest and during stress). In this technique, following the formation of a number of tags in the myocardium through spatially dependent excitation, a sequence of images is acquired at various phases of the cardiac cycle. In principle, many different tagging patterns can be generated through combinations of radio frequency (RF) excitation and gradient pulses. Considering its stability and efficiency, the conventional approach is to generate tagging in the Cartesian coordinate system by the spatial modulation of magnetization, known as SPAMM, in which the short alternating RF and gradient pulses generate a pattern of parallel lines in one or two directions. A similar approach to generate taglines in the presence of RF field inhomogeneities is based on the adiabatic delays alternating with nutations for tailored excitation (DANTE) inversion sequences.

The use of Cartesian tagging was bolstered with the development of the harmonic phase (HARP) concept. This concept considers the uniform and periodic pattern of taglines generated by SPAMM method, which is manifested in spectral peaks in the Fourier domain (k-space) at the fundamental frequency and harmonies of this repetition. The HARP concept helped in automation of the analysis of tagged images which has been a major problem in using tagging techniques for cardiac assessment.

Radial tagging is another pattern of interest that facilitates the measurement of angular information reflected in shear and twist of the left ventricle. Until the recent introduction of an effective pattern and efficient post processing method, this radial modulation of longitudinal magnetization was not being widely used due to the lack of an efficient preparation sequence to generate this tagging pattern robustly.

Yet another tagging pattern of interest is "ring" tagging shown in Spiegel, M. RingTag: ring-shaped tagging for myocardial centerline assessment. Invest Radiol 2003, 38(10):669-78. However, this method selectively excites on-resonance spins over a single curved line (e.g. one singular ring) by shifting the saturation plane off-center (e.g. with an RF pulse having an off-center frequency) and rotating it about an off-plane center point.

Additional background information relating to MRI and CMR can be found in the background art, such as U.S. Pat. Nos. 4,953,554; 5,054,489 5,111,820; 5,217,016; 6,453,187; 6,892,089; and 8,073,523; each of which is incorporated herein by reference in its entirety.

BRIEF SUMMARY OF THE INVENTION

The present invention provides methods, apparatus and systems for circular tagging in cardiac magnetic resonance imaging. A method is disclosed for spatial alteration of spin magnetization for creating a pattern of curvilinear tags in a target volume of an object being affected by NMR. In a preferred embodiment, the present invention is configured for imaging myocardial motion within the plane of the image by using a rotating excitation plane to produce a pattern of circular or curvilinear lines of altered magnetization, the motion of which can then be followed. The curvilinear spatial pattern of altered magnetization that is generated within the image region via the systems and methods of the present invention is particularly useful for studying motion and other physiological parameters within the heart.

Circular tagging according to an aspect of the invention is more adaptive to the natural geometry and the motion of the heart in general and, particularly, the left ventricle. The circular tagging technique of the present invention can be used to measure the mechanical parameters of the heart, such as wall thickening, radial strain and other physiological parameters.

In comparison with existing tagging techniques, circular tagging is advantageous for measuring the radial strain of myocardium. Circular tagging is also superior to Cartesian tagging since it is generated in the polar coordinate system and, therefore, does not require the transformation of measurements from Cartesian coordinate system to the polar coordinate system necessary for adapting the measurements for clinical practice. In addition, circular tagging is more compatible with the heart morphology and movement and, therefore, does not distort taglines as much as it happens with Cartesian tagging techniques. Furthermore, circular tagging is adaptive to simpler mathematical algorithms that make it easier for automatic calculations.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 shows a schematic diagram of a circular tagging NMR imaging system in accordance with the present invention.

FIG. 2 is an illustration of a rotating on-resonance excitation plane in relation to the imaging plane of the present invention.

FIGS. 5A through 5E show the state of magnetization for different times illustrated in the line tagging preparation sequence of FIG. 4.

DETAILED DESCRIPTION OF THE INVENTION

Figure 3:
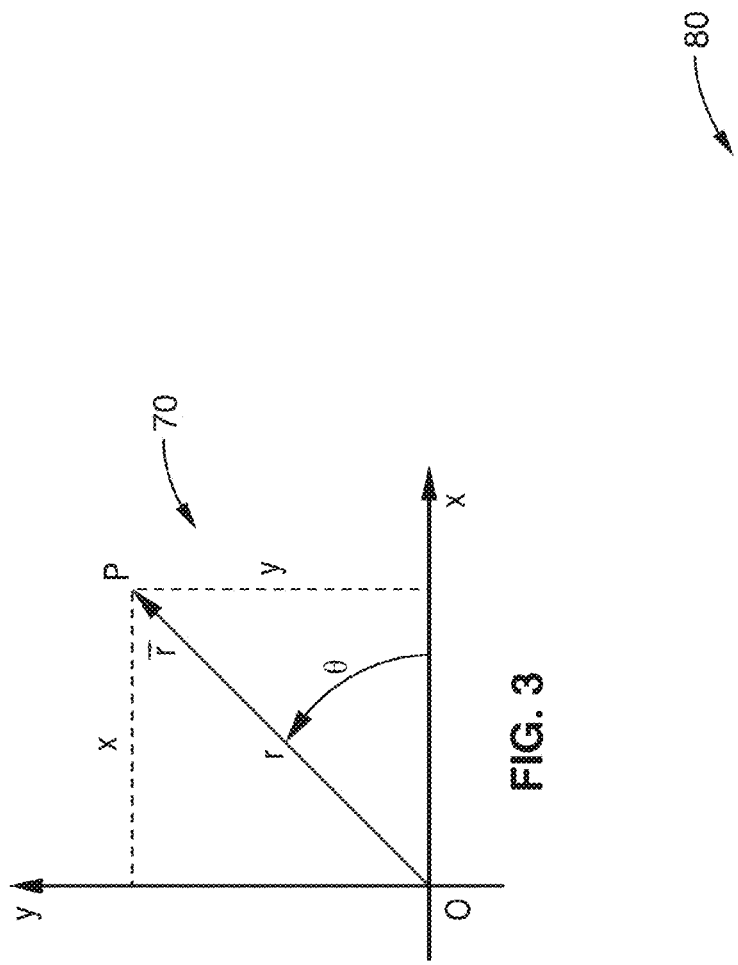
FIG. 3 is a diagram of a polar coordinate system.

FIG. 1 shows a schematic diagram of a circular tagging NMR system 10 in accordance with the present invention. System 10 is preferably configured to provide circular or curvilinear tagged NMR evaluation of tissue through the absorption and emission of energy of the radio frequency (RF) range of the electromagnetic spectrum.

Circular tagging NMR system 10 generally comprises a MRI scanner 12 that is coupled to a controls module 26 and one or more computers 30 containing software modules for operating the scanner 12 and controls module 26.

In a preferred embodiment, the circular tagging NMR system 10 comprises an imaging system configured to generate circular or curvilinear tags in magnetic resonance images (MRI) of a target volume of a particular object or anatomical feature of interest. However, it is appreciated the circular/curvilinear tags generated by the system and methods of the present invention may also be used for other NMR evaluation techniques.

MRI scanner 12 generally comprises an imaging magnet 14 for generating a primary magnetic field $B_o$ along central axis or iso-center 24 of bore 22. The imaging magnet 14 preferably comprises a superconducting magnet having a plurality of coils or windings of wire through which a current of electricity is passed to create the magnetic field (e.g. up to 2.0 tesla or more). In a preferred embodiment, the superconducting magnet 14 has near-zero resistance in the wires by maintaining the wires at cryogenic temperatures with liquid helium.

In addition to the imaging magnet 14, the MRI machine also contains a plurality of gradient generating magnets or coils 16. Gradient coils 16 have a much lower magnetic field than imaging magnet 14, and are used to create a variable field. Gradient coils 16 may comprise coils configured to produce deliberate variations in the main magnetic field ($B_o$) so that selective spatial excitation of the imaging volume can occur. In one embodiment, gradient coils 16 comprise three sets of orthogonally-oriented gradient coils, one for each direction. The variation in the magnetic field, or gradient, permits localization of image slices as well as phase encoding and frequency encoding. Gradients may also be used to apply reversal pulses for some imaging techniques.

The scanner 12 further comprises RF coils 18 that act as the "antenna" of the scanner by broadcasting RF signals to the patient and/or receive return signals from the patient. RF coils 18 are used to create an RF field which rotates the net magnetization in a pulse sequence, and also detect transverse magnetization. It is appreciated that the scanner 12 illustrated in FIG. 1 is for illustrative purposes only, and that the RF coils 18 and gradient coils 16 may comprise a number of different configurations.

When placed in a large magnetic field $B_o$, hydrogen atoms present in the human body have a strong tendency to align in the direction of the magnetic field. Inside the bore 22 of the scanner 12, the magnetic field $B_o$ runs down the center 24 of the tube in which the patient is placed (e.g. on table 20), so the hydrogen protons will line up in either the direction of the feet or the head. The majority will cancel each other, but the net number of protons is sufficient to produce an image.

To image, MRI scanner 12 applies radio frequency (RF) pulses that are specific to hydrogen through an RF coil 18 that is generally configured for the part of the body being scanned. The gradient coils 16 are rapidly turned on and off which alters the main magnetic field. The pulse directed to a specific area of the body causes the protons to absorb energy and spin in different direction, which is known as resonance. The resonance frequency, $w_0$, is referred to as the Larmor frequency, and RF coils 18 used for imaging are generally designed to resonate, or efficiently store energy, at the Larmor frequency.

On a macroscopic level, exposure of tissue to RF radiation at the Larmor frequency causes the net magnetization to spiral away from the $B_o$ field. In the rotating frame of reference, the net magnetization vector rotate from a longitudinal position a distance proportional to the time length of the RF pulse. After a certain length of time, the net magnetization vector rotates 90 degrees and lies in the transverse or x-y plane. It is in this position that the net magnetization can be detected on MRI scanner. The angle that the net magnetization vector rotates is commonly called the 'flip' or 'tip' angle. At angles greater than or less than 90 degrees there will still be a small component of the magnetization that will be in the x-y plane, and therefore be detected.

When the RF pulse is turned off the hydrogen protons slowly return to their natural alignment within the magnetic field $B_o$ and release their excess stored energy. This process, referred to as relaxation, may then be received by the RF coil 18 and sent to the computer 30 for processing via the processor 32. The received signal is sinusoidal in nature and is converted through the use of a Fourier transform (e.g. via image reconstruction software module 36) into an image.

To operate the scanner, one or more computers 30 send instructions to a controller 26, which then controls the individual components on the scanner 12 and amplifies the signals from the computer 30. The preparation sequence module 34 shapes the RF pulses and sets the shape and amplitude of each of the gradient fields.

The preparation sequence module 34 is of particular interest to the methods and systems of the invention, as the generated circular tag lines are a function of the instructions sent by the preparation sequence module 34 to the RF coils 18 and gradient coils 16.

Referring to FIG. 2, a particular aspect of the preparation sequence of the present invention is the ability to generate substantially parallel, concentric, curvilinear lines via a rotating "on-resonance" excitation plane 52 that is orthogonal to or oblique to the imaging plane 50. The term "on-resonance excitation plane" is herein defined as a rotating excitation plane in which the RF signal is on-resonance with the Larmor frequency of spins. The center 56 (corresponding with rotation axis 55) of on-resonance rotating plane 52 remains fixed (and preferably coincides with the image plane 50 center $I_c$), such that the on-resonance excitation plane 52 rotates about center 56, $I_c$ with a spin axis 55 that is fixed in an orientation orthogonal to or oblique to the imaging plane 50 (e.g. similar to the spin of a propeller). Thus, a point 58 within tissue 54 (and all points along ray r from the image center $I_c$), will be on-resonance twice every full rotation of the excitation plane 52, based on the rotating intersection of planes 50 and 52. For generating circular tags or taglines within a target volume 54, the spin axis 55 of the excitation plane 52 is orthogonal to, or substantially orthogonal to, the imaging plane.

The concentric circular tagging lines of the present invention are particularly useful in that they are generated in the polar coordinate system and, therefore, do not require the transformation of measurements from Cartesian coordinate system.

FIG. 3 illustrates a diagram of a polar coordinate system 70, wherein point on a plane is determined by a distance from a fixed point and an angle from a fixed direction. The fixed point O (analogous to the origin of a Cartesian system) is called the pole, and the ray from the pole in the fixed direction is the polar axis. The distance from the pole is referred to as the radial coordinate or radius r, and the angle Θ is referred to as the angular coordinate, polar angle, or azimuth.

Since the polar coordinate system adapts best to the morphology of the heart, cardiac strain is expressed in this coordinate system. Therefore, tagging the myocardium in the radial and circular directions helps not only in having a better intuition about the angular information reflected in shear and twist of the left ventricle, but also facilitates the calculation of strain with no need to the transformation of measurements from Cartesian coordinate system to the polar coordinate system.

Figure 4:
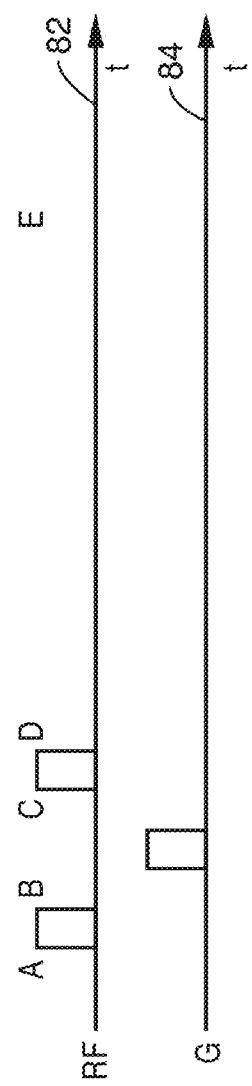
FIG. 4 illustrates a prior art preparation sequence used for line tagging.

FIG. 4 shows a timing diagram of a preparation pulse sequence 80 over time t for the prior art line-tagging SPAMM technique, wherein RF refers to the radio frequency excitation, and G refers to the wrap gradient for production of modulation. FIGS. 5A through 5E show the state of magnetization for different times illustrated in the line tagging preparation sequence of FIG. 4. In this technique, a series of parallel, straight tagging lines are generated by a sequence 80 of two non-selective, low energy RF pulses 82 that are separated by a magnetic field gradient pulse "wrap gradient" 84.

Figure 6:
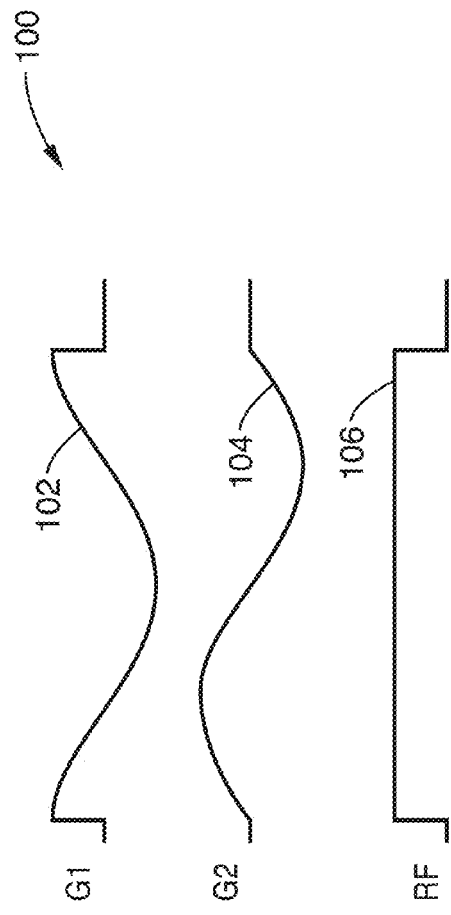
FIG. 6 is an illustration of a preparation pulse sequence and its constituents for circular/polar tagging according to an embodiment of the invention.

Referring now to FIG. 6, the constituents of a preparation pulse 100 for curvilinear tagging according to an embodiment of the invention are shown. The preparation pulse 100 comprises a sinusoidal two-dimensional gradient field represented by sinusoidal gradient pulses G 1 102 and G 2 104, which are generated simultaneously with a continuous (and generally smooth or constant) radio frequency signal 106. It is appreciated that the gradient pulses G 1 102 and G 2 104 may comprise an alternating waveform that is not sinusoidal, e.g. the gradient pulse may be any number of complex or periodic waveforms. For circular tagging, the RF pulse 106 is a small constant pulse that continues for a relatively long period of time in which the excitation plane can make a full rotation.

The preparation sequence module 34 is configured to generate preparation pulse 100 to control the output from gradient coils 16 and RF coils 18. The G1 and G2 pulses (102, 104) correspond to gradient pulses in specified directions (e.g. two of x, y, and z directions, or components thereof) corresponding to the imaging plane 50 and anatomy of interest. The preparation sequence module 34 also sends a continuous RF signal 106 to the RF coils 18 simultaneously with the gradient signals (102, 104) sent to gradient coils 16.

It is appreciated that the characteristics of preparation pulse 100 may be modified (e.g. magnitude, shape, etc.) to vary the orientation and shape of the generated curvilinear tagging lines within image plane 50. For example, the magnitude or phasor ($G_o$) of the G1 and G2 signals may be constant to generate circular-shaped tag lines (along with an excitation plane rotation axis 55 that is orthogonal to the imaging plane 50).

Alternatively, the RF signal 106 and the G1 and G2 signals may be varied (along with an excitation plane rotation axis 55) to generate elliptical or other curvilinear shapes. In all cases, the curvilinear lines are substantial and simultaneously generated within the target volume 54. The preparation sequence module 34 is also configured to shift the image center $I_c$ of the tagging pattern away from the iso-center 24 of the bore 22 according to the desired anatomical target (e.g. left ventricle of the heart). It is important to note, however, that the rotation axis 55 of the on-resonance plane 52 remain fixed (e.g. substantially coincident with the image center $I_c$) within the on-resonance plane during rotation of the on-resonance plane 56. This is in contrast to "ring" tagging where a singular ring tagline is generated from motion/rotation of an on-resonance plane axis.

Figure 7:
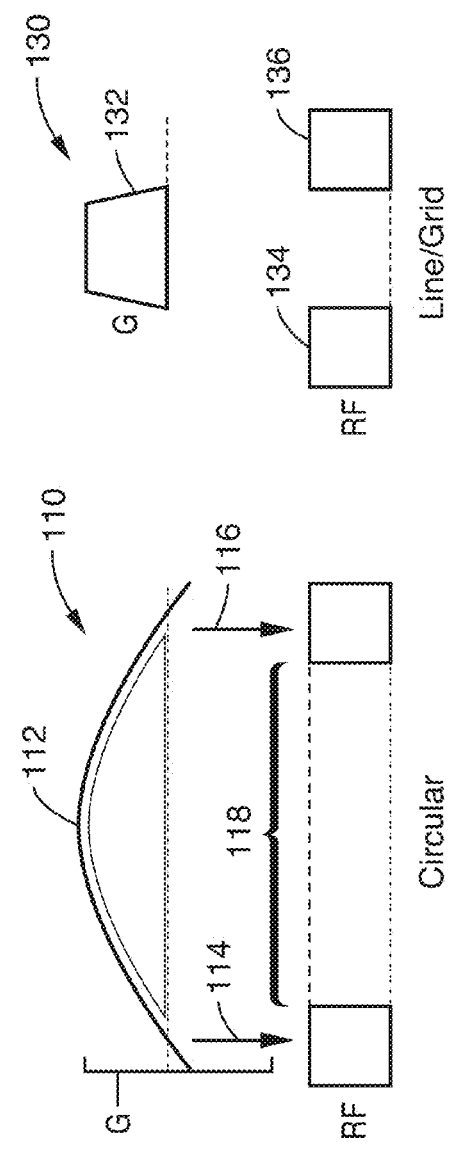
FIG. 7 is a comparison of the circular pulse sequence of the present invention with a line tagging pulse sequence.

FIG. 7 illustrates a comparison of the circular pulse sequence 110 of the present invention with a line tagging pulse sequence 130 according to SPAMM. It is important to note that the G and RF signals of circular sequence 110 are illustrated for a point or series of points along a ray r corresponding to the intersection of the on-resonance plane 52 with the imaging plane 50 (see FIG. 2), whereas the pulsed G signals 132 and RF signals 134, 136 of line tagging pulse sequence 130 are simultaneously and universally generated on all points in the imaging plane. While the RF signal 106 (FIG. 6) is continuous, the dephasing gradient 112 of the circular sequence 110 generates a rotating on-resonance plane such that the RF on-resonance condition of the tissue 54 (e.g. frequency of RF pulse that matches resonant frequency $w_0$, or Larmor frequency, of the tissue) is experienced twice for the points along the ray r during the period corresponding to one full rotation of the on-resonance excitation plane. These points are illustrated in FIG. 7 with arrows shown as first on-resonance point 114 and second on-resonance point 116. The dashed line illustrates the dephasing or off-resonance period 118 manipulated by dephasing gradient 112. Thus, off-resonance effects and manipulation of phase have a significant role in the aforementioned excitation of the tissue.

FIGS. 8A through 8E illustrate an in-plane view of the imaging plane 50 centered about a target anatomical region 54 during saturation/preparation of the magnetization to generate a circular tagging pattern on the object tissue 54 being imaged. As explained previously, the circular tagging sequence 100 generates a rotating excitation plane 52 in combination with a continuous RF pulse, which can result in substantial excitation.

Figure 8A:
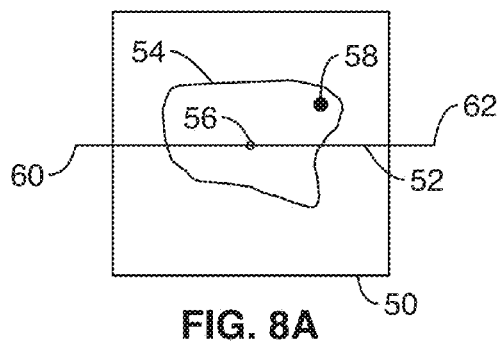
FIGS. 8A through 8E show points along a full rotation of the excitation plane within the imaging plane.
Figure 8B:
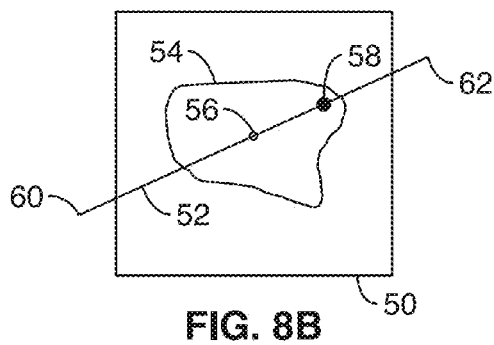
Figure 8C:
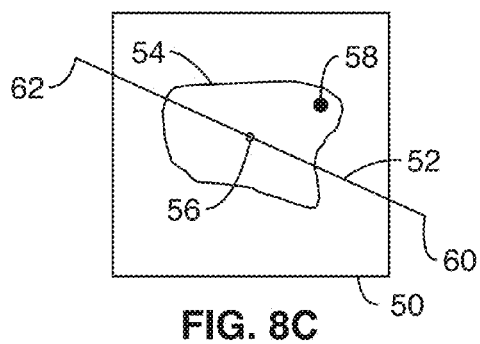
Figure 8D:
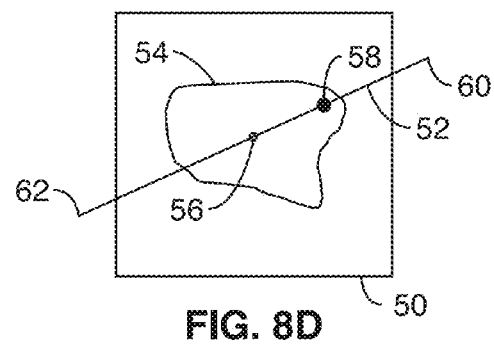
Figure 8E:
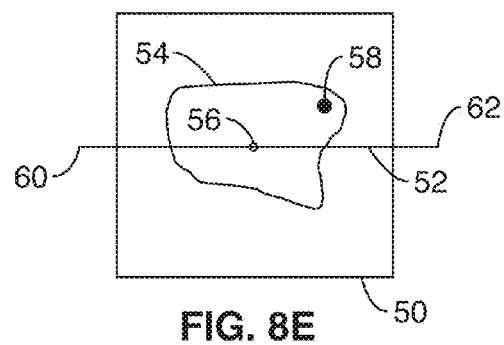

FIG. 8A illustrates a start of rotation for the on-resonance plane 52, as manipulated by gradient signals G1, G2 (102, 104 in FIG. 6). The plane 52 rotates about plane center 56, which is the midpoint between first end 60 and second end 62 of the plane.

For each full rotation of plane 52, each point (e.g. point 58) in the imaging plane will become on-resonance for two times. In the first on-resonance excitation for point 58 illustrated in FIG. 8B, there will be a considerable amount of excitation for each spin, as long as the magnitude of the RF 106 as well as the gradient magnetic fields G1, G2 are properly set. For the period between the first and second on-resonance time points shown in FIG. 8C, spins rotate several times because of the off-resonance excitation. Each spin therefore finds a specific phase at the time of its second on-resonance excitation shown for point 58 in FIG. 8D. This specific phase is a function of the distance of the point (e.g. point 58) from the center $I_c$ of the image (shown coincident with the plane center/rotation axis 58 in FIGS. 8A through 8E). In particular, this phase is equal for spins that have equal space from the center 58, and changes fast in the radial direction. The effect of second on-resonance excitation is a function of aforementioned phase, which determines if the new excitation increases or decreases the total amount of excitation angle.

FIGS. 9A through 9E and 10A through 10E show simulations of the transverse component of magnetization and phase of magnetization, respectively, through different points along one full rotation of the on-resonance plane (shown as the line in the image).

Figure 9B:
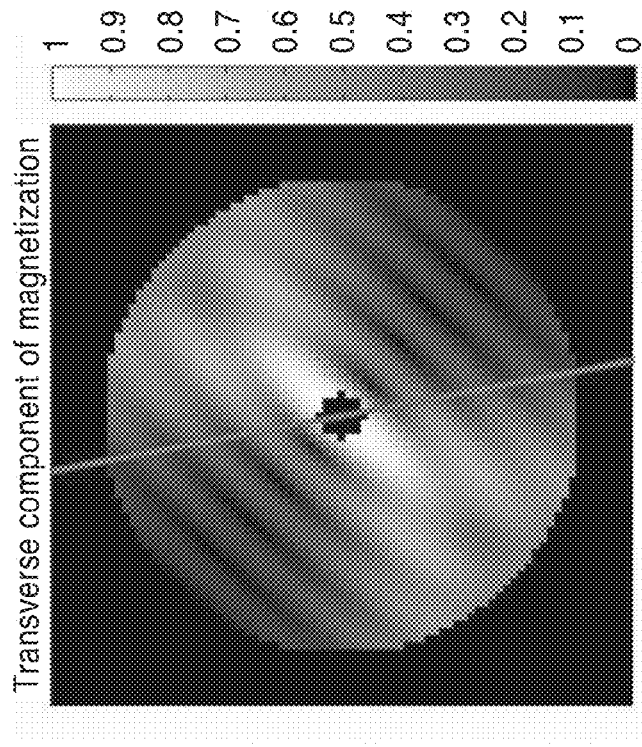
FIG. 9B shows the transverse component of magnetization with respect to the imaging plane after approximately 90° rotation.
Figure 9A:
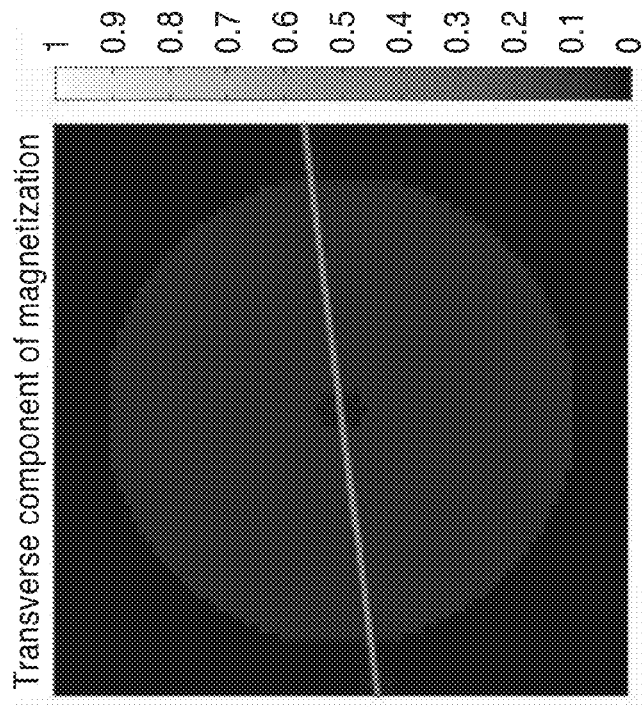
FIG. 9A shows the transverse component of magnetization with respect to the imaging plane prior to rotation.
Figure 9D:
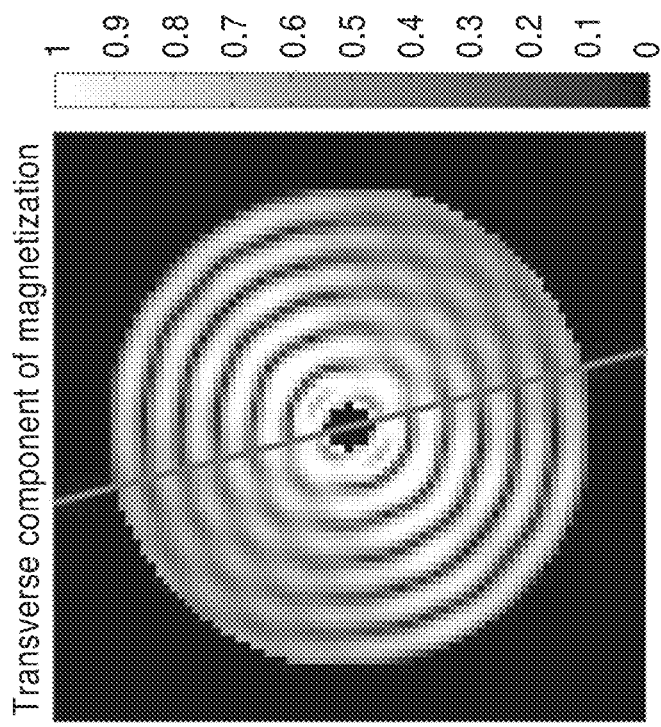
FIG. 9D shows the transverse component of magnetization with respect to the imaging plane after approximately 270° rotation.
Figure 9C:
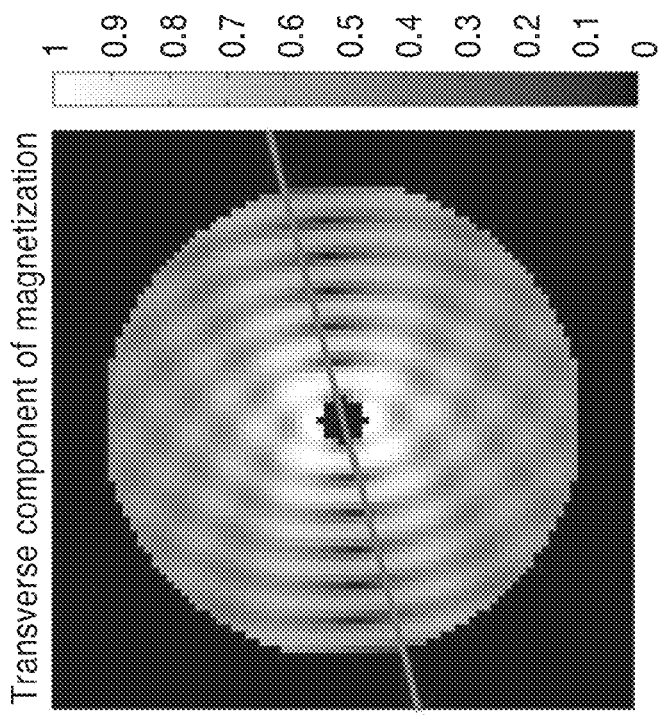
FIG. 9C shows the transverse component of magnetization with respect to the imaging plane after approximately 180° rotation.
Figure 9E:
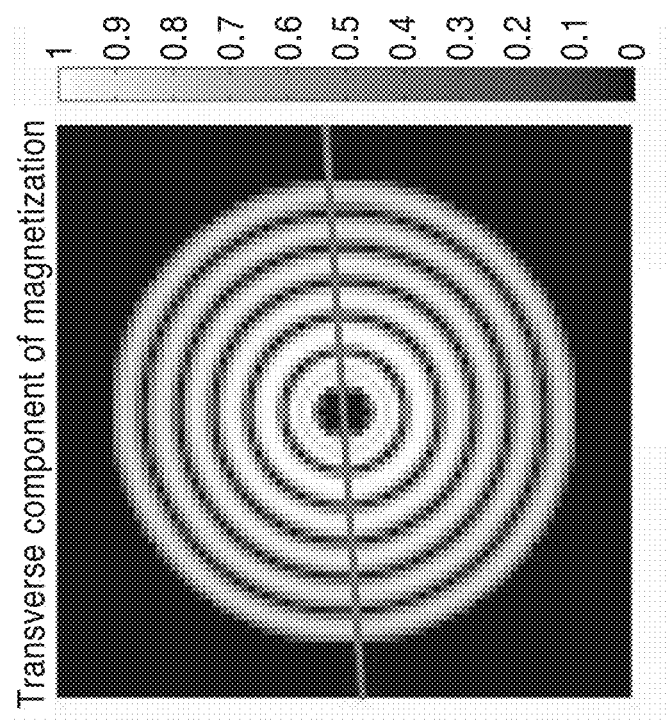
FIG. 9E shows the phase of magnetization with respect to the imaging plane after approximately one full rotation.

FIG. 9A shows the transverse component of magnetization with respect to the imaging plane prior to rotation. FIG. 9B shows the transverse component of magnetization with respect to the imaging plane after approximately 90° rotation. FIG. 9C shows the transverse component of magnetization with respect to the imaging plane after approximately 180° rotation. FIG. 9D shows the transverse component of magnetization with respect to the imaging plane after approximately 270° rotation. FIG. 9E shows the phase of magnetization with respect to the imaging plane after approximately one full rotation.

Figure 10B:
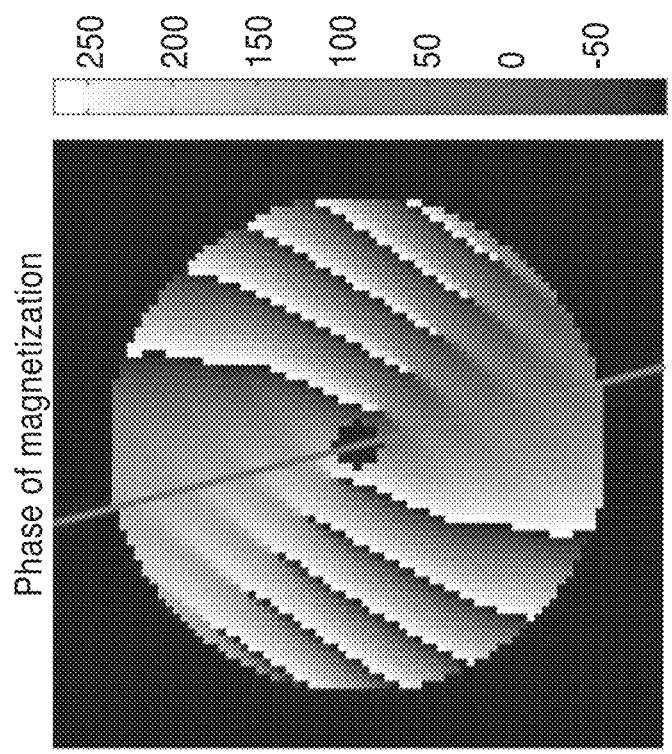
FIG. 10B shows the phase of magnetization with respect to the imaging plane after approximately 90° rotation.
Figure 10A:
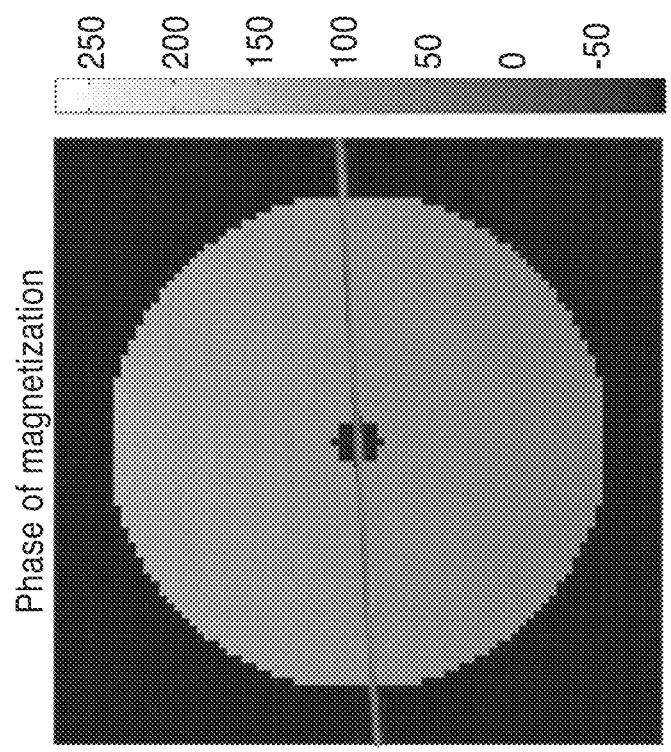
FIG. 10A shows the phase of magnetization with respect to the imaging plane prior to rotation.
Figure 10D:
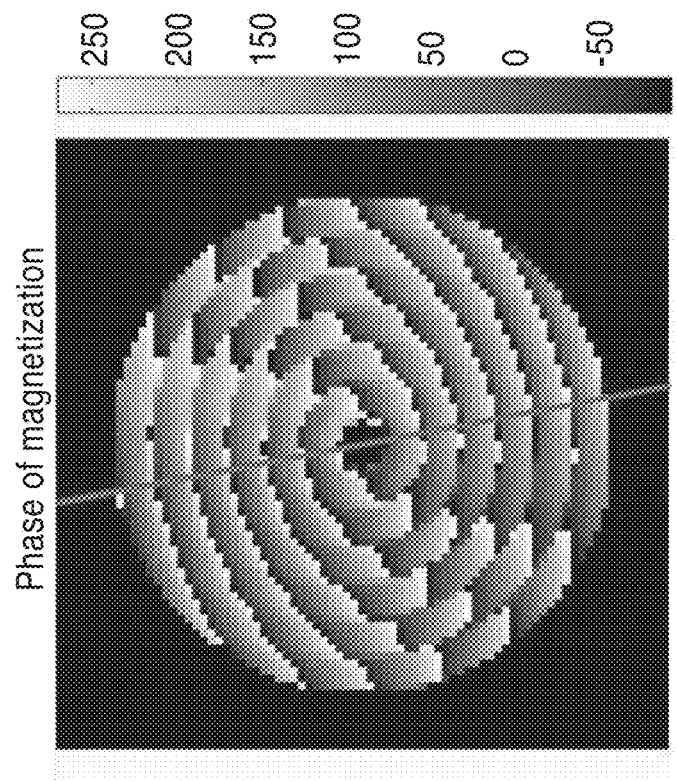
FIG. 10D shows the phase of magnetization with respect to the imaging plane after approximately 270° rotation.
Figure 10C:
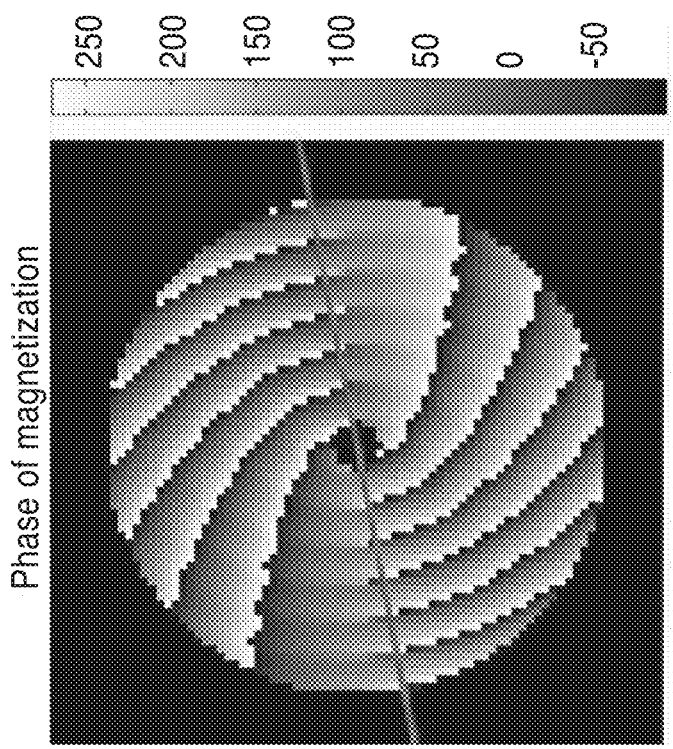
FIG. 10C shows the phase of magnetization with respect to the imaging plane after approximately 180° rotation.
Figure 10E:
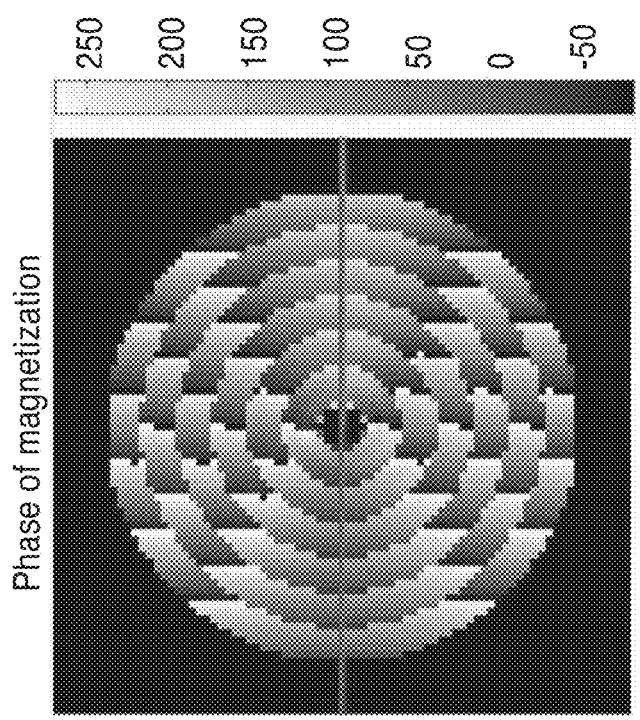
FIG. 10E shows the phase of magnetization with respect to the imaging plane after approximately one full rotation.

FIG. 10A shows the phase of magnetization with respect to the imaging plane prior to rotation. FIG. 10B shows the phase of magnetization with respect to the imaging plane after approximately 90° rotation. FIG. 10C shows the phase of magnetization with respect to the imaging plane after approximately 180° rotation. FIG. 10D shows the phase of magnetization with respect to the imaging plane after approximately 270° rotation. FIG. 10E shows the phase of magnetization with respect to the imaging plane after approximately one full rotation.

Referring back to FIG. 1, subsequent to the preparation/magnetization sequence generated by the preparation sequence module 34, imaging is performed (e.g. via RF coils 18) for reconstruction of the image by image reconstruction module 36 to generate an image of the anatomy 54 comprising the polar/circular tag lines.

A post processing module 38 may also be employed to evaluate physiological characteristics e.g. myocardial strain, etc. using the generated polar tag lines. In one embodiment, the circumferential compression encoding (CIRCOME) post-processing method may be employed to automatically calculate the global circumferential strain.

Figure 11:
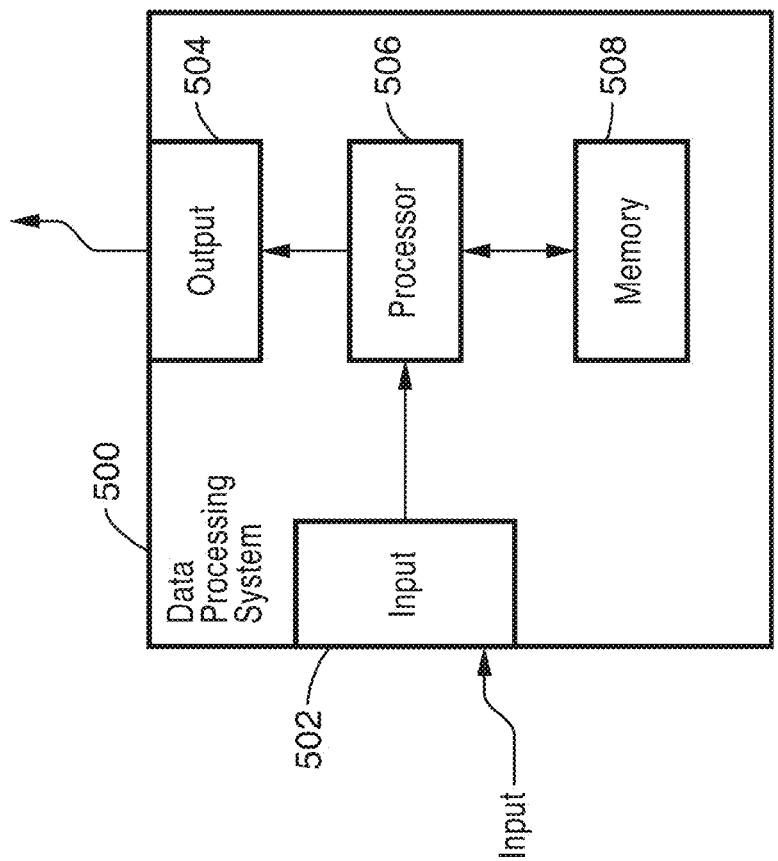
FIG. 11 illustrates a schematic diagram of an image processing module in accordance with the present invention.

By way of example, and not of limitation, a block diagram depicting the components of an MRI data processing system 500 employing circular tagging is provided in FIG. 11. The system 500 comprises an input 502 for receiving data regarding the images. The data input at 502 may comprise raw data acquired by the scanner 12 detector (e.g. RF coils 18) for image reconstruction via module 36, or may be the constructed image generated by the image reconstruction module 36 for post processing at module 38. Note that the input 502 may include multiple "ports." An output 504 is connected with the processor 506 for providing information to a user or to other systems such that a network of computer systems may serve as a system for obtaining physiological data (e.g. strain). Output may also be provided to other devices or other programs; e.g., to other software modules, for use therein (e.g. preparation sequence 34, image reconstruction 36 and post processing modules 38 may all be performed on separate computers 30). The input 502 and the output 504 are both coupled with a processor 506, which may be a general-purpose computer processor or a specialized processor designed specifically for use with the present invention. The processor 506 is coupled with a memory 508 to permit storage of data and software (e.g. one or more modules 32, 34, 36) that are to be manipulated by commands to the processor 506.

Figure 12:
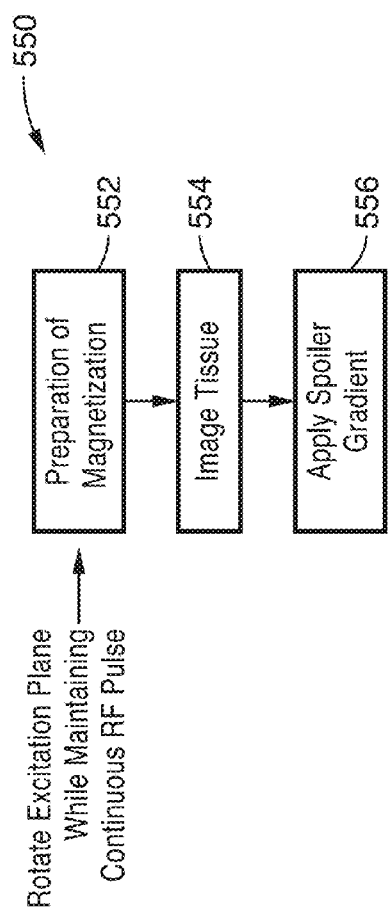
FIG. 12 illustrates a flow diagram of an imaging sequence in accordance with the present invention.

FIG. 12 illustrates an exemplary flow diagram of an imaging sequence 550 for generating an image having curvilinear/polar tag lines in accordance with the present invention. In the first block at step 552, the preparation sequence is generated (e.g. via module 32) having sinusoidal gradient signals G 1, G 2 applied over a continuous RF signal 106 to create a rotating on-resonance plane. At block 554, the preparation sequence is followed by a dynamic imaging module (e.g. module 34), such as spoiled gradient echo (GRE) cine readout to generate a tissue image having a tagging pattern with circular symmetry around the center of the image. Next at 556, a spoiler gradient is applied, which destroys the net transverse magnetization prior to the next imaging sequence.

EXAMPLE

The sequence shown in FIG. 6 was implemented using a commercial imaging platform, and tested on phantoms and applied on healthy volunteers. The time period needed for tagging depends on number of taglines and other factors. The tagging period ranged between about 25-30 ms in the current implementations, but can become shorter. Images were acquired by a 1.5 T scanner. Other MR parameters were as follows: 250 mm FOV, 5 mm slice thickness, 250 Hz/pixel, 15° flip angle, TE/TR=4.6/86 ms, and 256×256 matrix size. The actual implementation of these cine sequences was performed on a commercial imaging platform (Siemens Medical Solutions, Erlangen, Germany) by using developmental software (IDEA, VB17; Siemens Medical Solutions).

Figure 13C:
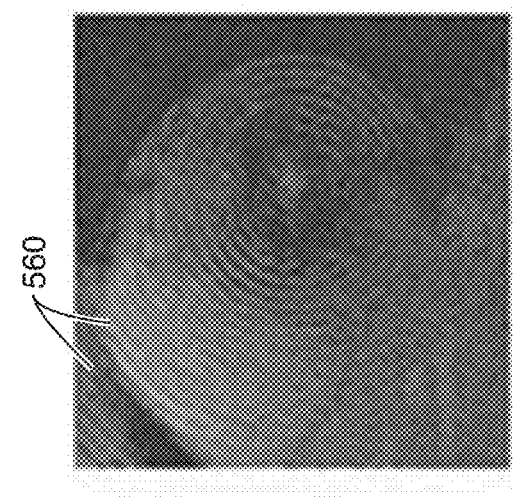
FIG. 13C is an image illustrating the results of using circular tagging on the heart of a healthy volunteer.
Figure 13B:
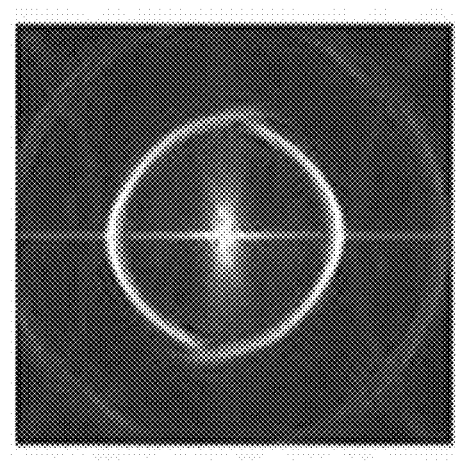
FIG. 13B is a K-Space representation of the phantom of FIG. 13A.
Figure 13A:
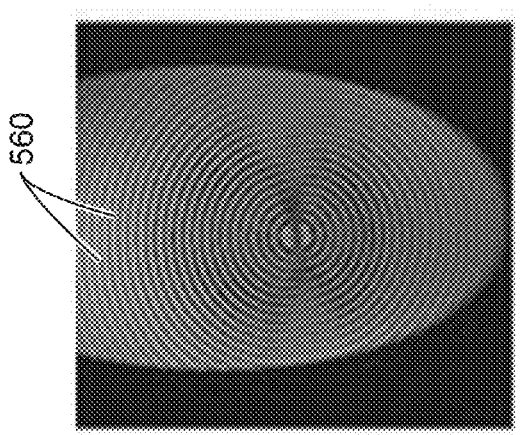
FIG. 13A is an image of circular tagging on a phantom.

Results are shown in FIG. 13. Image A is an image showing circular tagging on a phantom. Concentric, evenly-spaced, parallel, and substantially circular tagging lines 560 are shown. Image B is a picture showing the K-space representation corresponding to Image A. As can be seen, the K-space image B shows how the effect of circular tagging is well separated in this space. Panel C is a circularly tagged image of a healthy volunteer. Again, concentric, evenly-spaced, parallel, and substantially circular tagging lines 560 are shown.

As can be seen, a new tagging sequence has been designed and implemented. The sequence has been successfully tested on phantom and also used to acquire short axis images of the left ventricle of healthy volunteers. The spatial resolution and density of taglines were found to be considerably higher compared to previous schemes of the radial tagging, and allows for relatively simple derivation of myocardial shear rate and angular strain. Advantageously, circular tagging allows for displaying myocardial twist which cannot be displayed using radial tagging.

The invention can be included as part of the cardiac software package of MRI systems, so that assessment of the myocardium function through the wall thickening or wall motion can be added to the exam protocol. (Similar to the current practice of other cardiac MRI tagging techniques).

The manner of integrating circular tagging into the cardiac software package of an MRI would be readily apparent to one of ordinary skill in the art. The pulse sequence and imaging method would, for example, be embodied in the form of computer system 30 operating software (e.g. preparation sequence module 34) or in the form of a "hard-coded" instruction set in the cardiac software package. Circular tagging could also be embodied, for example, in the form of a separate computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula (e), or computational depiction(s).

From the discussion above it will be appreciated that the invention can be embodied in various ways, including the following:

1. A method for generating a pattern of curvilinear tags of altered magnetization in a target volume of an object being affected by NMR, the NMR generated from an NMR scanner having a magnetic field gradient generating coil and an RF coil, the method comprising: generating an alternating gradient signal to operate the magnetic field gradient generating coil; and generating a continuous radio frequency (RF) signal to operate the RF coil simultaneously with at least part of the alternating gradient signal; wherein the alternating gradient signal is shaped to generate a rotating on-resonance excitation plane; wherein the on-resonance excitation plane is configured such that each point in the target volume is on-resonance for at least two time points during a period corresponding to at least one full rotation of the on-resonance excitation plane; and wherein the rotating on-resonance excitation plane is configured to generate a plurality of curvilinear tags of altered magnetization within the target volume.

2. The method of embodiment 1: wherein the alternating gradient signal and radio frequency (RF) signal are generated as part of an NMR imaging preparation sequence; and wherein the curvilinear tags comprise curvilinear taglines within an imaging plane of an NMR image.

3. The method of embodiment 2, further comprising: controlling the gradient coil to deliver a gradient field corresponding to the alternating gradient signal into the object within the imaging plane; and simultaneously controlling the RF coil to deliver an RF field corresponding to the continuous RF signal; wherein the delivered gradient field and RF field alter the alignment of particles within the object.

4. The method of embodiment 2, wherein the curvilinear taglines comprise curvilinear lines of altered magnetization that are substantially equally spaced, substantially parallel, and substantially concentric.

5. The method of embodiment 2, wherein the rotating on-resonance excitation plane rotates on an axis substantially orthogonal to the imaging plane to simultaneously generate a plurality of circular taglines.

6. The method of embodiment 4, wherein the magnitude of the alternating gradient signal is constant to simultaneously generate a plurality of circular taglines.

7. The method of embodiment 2, wherein the rotating on-resonance excitation plane rotates on an axis oblique to the imaging plane to generate a plurality of elliptical taglines.

8. The method of embodiment 1, wherein the alternating gradient signal comprises a two-dimensional sinusoidal gradient signal.

9. The method of embodiment 2, wherein the rotation axis is substantially fixed with respect to the imaging plane during rotation of the on-resonance excitation plane.

10. The method of embodiment 8, wherein the rotation axis is substantially parallel to and lies substantially within the on-resonance excitation plane.

11. The method of embodiment 2, wherein the RF signal comprises a substantially constant signal.

12. The method of embodiment 3, further comprising: receiving data from the magnetized image plane corresponding to the altered alignment of particles within the object; and generating the NMR image from said data.

13. A preparation sequencing apparatus for generating curvilinear tags of altered magnetization in a target volume of an object being affected by NMR, comprising: a processor; and programming executable on said processor for: generating an alternating gradient signal; and generating a continuous radio frequency (RF) signal simultaneously with the alternating gradient signal; wherein the alternating gradient signal is shaped to generate a rotating on-resonance excitation plane; wherein the on-resonance excitation plane is configured such that each point in the target volume is on-resonance for at least two time points during a period corresponding to at least one full rotation of the on-resonance excitation plane; and wherein the rotating on-resonance excitation plane is configured to simultaneously generate a plurality of curvilinear tags of altered magnetization in the target volume.

14. The apparatus of embodiment 13, wherein the preparation sequencing apparatus is configured for generating curvilinear taglines within an imaging plane of an NMR image.

15. The apparatus of embodiment 14, wherein the curvilinear taglines comprise curvilinear regions of altered magnetization that are substantially equally spaced, substantially parallel, and substantially concentric.

16. The apparatus of embodiment 14, wherein the rotating on-resonance excitation plane rotates on an axis substantially orthogonal to the imaging plane to simultaneously generate a plurality of circular taglines.

17. The apparatus of embodiment 16, wherein the magnitude of the alternating gradient signal is constant to simultaneously generate a plurality of circular taglines.

18. The apparatus of embodiment 14, wherein the rotating on-resonance excitation plane rotates on an axis oblique to the imaging plane to generate a plurality of elliptical taglines.

19. The apparatus of embodiment 13, wherein the alternating gradient signal comprises a two-dimensional sinusoidal gradient signal.

20. The apparatus of embodiment 14, wherein the rotation axis is substantially fixed with respect to the imaging plane during rotation of the on-resonance excitation plane.

21. The apparatus of embodiment 20, wherein the rotation axis is substantially parallel to and lies substantially within the on-resonance excitation plane.

22. The apparatus of embodiment 14, wherein the RF signal comprises a substantially constant signal.

23. An NMR imaging system for generating an NMR image comprising curvilinear taglines of altered magnetization within an imaging plane corresponding to the NMR image, comprising: a magnetic field gradient generating coil; an RF coil; and a preparation sequencing module for generating a preparation sequence to control the gradient generating coil and RF coil; the preparation sequence configured to generate a alternating gradient signal to operate the gradient generating coil, and a continuous a radio frequency (RF) signal to operate the RF coil simultaneously with the alternating gradient signal; wherein the alternating gradient signal is shaped to generate a rotating on-resonance excitation plane such that each point in the target volume is on-resonance for at least two time points during a period corresponding to at least one full rotation of the on-resonance excitation plane; and wherein the rotating on-resonance excitation plane is configured to generate a plurality of curvilinear taglines of altered magnetization in the imaging plane.

24. The system of embodiment 23, wherein the curvilinear taglines comprise curvilinear regions of altered magnetization that are substantially equally spaced, substantially parallel, and substantially concentric.

25. The system of embodiment 23, wherein the rotating on-resonance excitation plane rotates on an axis substantially orthogonal to the imaging plane to simultaneously generate a plurality of circular taglines.

26. The system of embodiment 25, wherein the magnitude of the alternating gradient signal is constant to simultaneously generate a plurality of circular taglines.

27. The system of embodiment 23, wherein the rotating on-resonance excitation plane rotates on an axis oblique to the imaging plane to generate a plurality of elliptical taglines.

28. The system of embodiment 23, wherein the alternating gradient signal comprises a two-dimensional sinusoidal gradient signal.

29. The system of embodiment 23, wherein the rotation axis is substantially fixed with respect to the imaging plane during rotation of the on-resonance excitation plane.

30. The system of embodiment 23, wherein the preparation sequencing module comprises: a processor; and programming executable on said processor for generating the preparation sequence.

31. The system of embodiment 23, further comprising: an imaging module; the imaging module configured for receiving data from the magnetized image plane and generating an image from said data.

32. A non-transitory computer readable media containing instructions executable on a computer for carrying out a method for generating curvilinear tags of altered magnetization in a target volume of an object being affected by NMR, the method comprising: generating an alternating gradient signal; and generating a continuous radio frequency (RF) signal simultaneously with the alternating gradient signal; wherein the alternating gradient signal is shaped to generate a rotating on-resonance excitation plane; wherein the on-resonance excitation plane is configured such that each point in the target volume is on-resonance for at least two time points during a period corresponding to at least one full rotation of the on-resonance excitation plane; and wherein the rotating on-resonance excitation plane is configured to simultaneously generate a plurality of curvilinear tags of altered magnetization in the target volume.

Although the description above contains many details, these should not be construed as limiting the scope of the invention but as merely providing illustrations of some of the presently preferred embodiments of this invention. For example, the system and methods disclosed herein are directed to imaging of human or non-human (e.g. animal) tissue, and in particular myocardial tissue. However, it is appreciated that the systems and methods of the present invention may also be used for imaging of inanimate or non-living objects.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for generating a pattern of curvilinear tags of altered magnetization in a target volume of an object being affected by NMR, the NMR generated from an NMR scanner having a magnetic field gradient generating coil and an RF coil, the method comprising:
generating an alternating gradient signal to operate the magnetic field gradient generating coil; and
generating a continuous radio frequency (RF) signal to operate the RF coil simultaneously with at least part of the alternating gradient signal;
wherein the alternating gradient signal is shaped to generate a rotating on-resonance excitation plane;
wherein the on-resonance excitation plane is configured such that each point in the target volume is on-resonance for at least two time points during a period corresponding to at least one full rotation of the on-resonance excitation plane;
wherein the rotating on-resonance excitation plane is configured to generate a plurality of curvilinear tags of altered magnetization within the target volume; and
generating an output image of the target volume comprising the curvilinear tags.

2. A method as recited in claim 1:
wherein the alternating gradient signal and radio frequency (RF) signal are generated as part of an NMR imaging preparation sequence; and
wherein the curvilinear tags comprise curvilinear taglines within an imaging plane of an NMR image.

3. A method as recited in claim 2, further comprising:
controlling the gradient coil to deliver a gradient field corresponding to the alternating gradient signal into the object within the imaging plane; and
simultaneously controlling the RF coil to deliver an RF field corresponding to the continuous RF signal;
wherein the delivered gradient field and RF field alter the alignment of particles within the object.

4. A method as recited in claim 2, wherein the curvilinear taglines comprise curvilinear lines of altered magnetization that are substantially equally spaced, substantially parallel, and substantially concentric.

5. A method as recited in claim 2, wherein the rotating on-resonance excitation plane rotates on an axis substantially orthogonal to the imaging plane to simultaneously generate a plurality of circular taglines.

6. A method as recited in claim 4, wherein the magnitude of the alternating gradient signal is constant to simultaneously generate a plurality of circular taglines.

7. A method as recited in claim 2, wherein the rotating on-resonance excitation plane rotates on an axis oblique to the imaging plane to generate a plurality of elliptical taglines.

8. A method as recited in claim 1, wherein the alternating gradient signal comprises a two-dimensional sinusoidal gradient signal.

9. A method as recited in claim 2, wherein the rotation axis is substantially fixed with respect to the imaging plane during rotation of the on-resonance excitation plane.

10. A method as recited in claim 8, wherein the rotation axis is substantially parallel to and lies substantially within the on-resonance excitation plane.

11. A method as recited in claim 2, wherein the RF signal comprises a substantially constant signal.

12. A method as recited in claim 3, further comprising:
receiving data from the magnetized image plane corresponding to the altered alignment of particles within the object; and
generating the NMR image from said data.

13. A preparation sequencing apparatus for generating curvilinear tags of altered magnetization in a target volume of an object being affected by NMR, comprising:
a processor; and
programming executable on said processor for:
generating an alternating gradient signal;
generating a continuous radio frequency (RF) signal simultaneously with the alternating gradient signal;
wherein the alternating gradient signal is shaped to generate a rotating on-resonance excitation plane;

wherein the on-resonance excitation plane is configured such that each point in the target volume is on-resonance for at least two time points during a period corresponding to at least one full rotation of the on-resonance excitation plane; and wherein the rotating on-resonance excitation plane is configured to simultaneously generate a plurality of curvilinear tags of altered magnetization in the target volume; and generating an output image of the target volume comprising the curvilinear tags.

14. An apparatus as recited in claim 13, wherein the preparation sequencing apparatus is configured for generating curvilinear taglines within an imaging plane of an NMR image.

15. An apparatus as recited in claim 14, wherein the curvilinear taglines comprise curvilinear regions of altered magnetization that are substantially equally spaced, substantially parallel, and substantially concentric.

16. An apparatus as recited in claim 14, wherein the rotating on-resonance excitation plane rotates on an axis substantially orthogonal to the imaging plane to simultaneously generate a plurality of circular taglines.

17. An apparatus as recited in claim 16, wherein the magnitude of the alternating gradient signal is constant to simultaneously generate a plurality of circular taglines.

18. An apparatus as recited in claim 14, wherein the rotating on-resonance excitation plane rotates on an axis oblique to the imaging plane to generate a plurality of elliptical taglines.

19. An apparatus as recited in claim 13, wherein the alternating gradient signal comprises a two-dimensional sinusoidal gradient signal.

20. An apparatus as recited in claim 14, wherein the rotation axis is substantially fixed with respect to the imaging plane during rotation of the on-resonance excitation plane.

21. An apparatus as recited in claim 20, wherein the rotation axis is substantially parallel to and lies substantially within the on-resonance excitation plane.

22. An apparatus as recited in claim 14, wherein the RF signal comprises a substantially constant signal.

23. An NMR imaging system for generating an NMR image comprising curvilinear taglines of altered magnetization within an imaging plane corresponding to the NMR image, comprising:
   a magnetic field gradient generating coil;
   an RF coil; and
   a preparation sequencing module for generating a preparation sequence to control the gradient generating coil and RF coil;
   the preparation sequence configured to generate a alternating gradient signal to operate the gradient generating coil, and a continuous a radio frequency (RF) signal to operate the RF coil simultaneously with the alternating gradient signal;
   wherein the alternating gradient signal is shaped to generate a rotating on-resonance excitation plane such that each point in the target volume is on-resonance for at least two time points during a period corresponding to at least one full rotation of the on-resonance excitation plane; and
   wherein the rotating on-resonance excitation plane is configured to generate a plurality of curvilinear taglines of altered magnetization in the imaging plane.

24. A system as recited in claim 23, wherein the curvilinear taglines comprise curvilinear regions of altered magnetization that are substantially equally spaced, substantially parallel, and substantially concentric.

25. A system as recited in claim 23, wherein the rotating on-resonance excitation plane rotates on an axis substantially orthogonal to the imaging plane to simultaneously generate a plurality of circular taglines.

26. A system as recited in claim 25, wherein the magnitude of the alternating gradient signal is constant to simultaneously generate a plurality of circular taglines.

27. A system as recited in claim 23, wherein the rotating on-resonance excitation plane rotates on an axis oblique to the imaging plane to generate a plurality of elliptical taglines.

28. A system as recited in claim 23, wherein the alternating gradient signal comprises a two-dimensional sinusoidal gradient signal.

29. A system as recited in claim 23, wherein the rotation axis is substantially fixed with respect to the imaging plane during rotation of the on-resonance excitation plane.

30. A system as recited in claim 23, wherein the preparation sequencing module comprises:
   a processor; and
   programming executable on said processor for generating the preparation sequence.

31. A system as recited in claim 23, further comprising:
   an imaging module;
   the imaging module configured for receiving data from the magnetized image plane and generating an image from said data.

32. A non-transitory computer readable media containing instructions executable on a computer for carrying out a method for generating curvilinear tags of altered magnetization in a target volume of an object being affected by NMR, the method comprising:
   generating an alternating gradient signal; and
   generating a continuous radio frequency (RF) signal simultaneously with the alternating gradient signal;
   wherein the alternating gradient signal is shaped to generate a rotating on-resonance excitation plane;
   wherein the on-resonance excitation plane is configured such that each point in the target volume is on-resonance for at least two time points during a period corresponding to at least one full rotation of the on-resonance excitation plane;
   wherein the rotating on-resonance excitation plane is configured to simultaneously generate a plurality of curvilinear tags of altered magnetization in the target volume; and
   generating an output image of the target volume comprising the curvilinear tags.

* * * * *